(12) United States Patent
Hoshino (10) Patent No.: US 8,813,553 B2
(45) Date of Patent: Aug. 26, 2014

(54) DEVICE FOR PEEL TEST (75) Inventor: Yoshinori Hoshino, Saitama (JP)

(73) Assignee: Kyowa Interface Science Co., Ltd., Saitama (JP)

( * ) Notice: Subject to any disclaimer, the term of this patent is extended or adjusted under 35 U.S.C. 154(b) by 379 days.

(21) Appl. No.: 13/285,191

(22) Filed: Oct. 31, 2011

(65) Prior Publication Data
US 2012/0103081 A1 May 3, 2012

(30) Foreign Application Priority Data

Nov. 1, 2010 (JP) ................................. 2010-245282

(51) Int. Cl.
*G01N 19/04* (2006.01)
*G01N 3/08* (2006.01)

(52) U.S. Cl.
CPC ........ *G01N 19/04* (2013.01); *G01N 2203/0025* (2013.01); *G01N 2203/0605* (2013.01)
USPC .......................................... 73/150 A; 73/827

(58) Field of Classification Search
CPC .......... G01N 19/04; G01N 2203/0605; G01N 2203/0025
USPC ..................... 73/150 A, 150 R, 827
See application file for complete search history.

(56) References Cited

U.S. PATENT DOCUMENTS

| | | | | |
|---|---|---|---|---|
| 2,751,784 A | * | 6/1956 | Gershberg | 73/150 A |
| 2,752,780 A | * | 7/1956 | Gershberg | 73/150 A |
| 3,282,309 A | * | 11/1966 | Parker et al. | 29/27 A |
| 3,473,676 A | * | 10/1969 | Cotney | 221/293 |
| 3,580,065 A | * | 5/1971 | Strittmater et al. | 73/150 R |
| 4,785,657 A | * | 11/1988 | Votava | 72/405.14 |
| 4,893,513 A | * | 1/1990 | Schroeder et al. | 73/150 A |
| 5,072,238 A | * | 12/1991 | Takamiya et al. | 347/198 |
| 5,109,597 A | * | 5/1992 | Elder et al. | 29/755 |
| 5,404,751 A | * | 4/1995 | Beran et al. | 73/150 A |
| 5,438,863 A | * | 8/1995 | Johnson | 73/150 A |
| 5,596,133 A | * | 1/1997 | Maciejewski | 73/150 A |

(Continued)

FOREIGN PATENT DOCUMENTS

JP 1997113438 A 5/1997

OTHER PUBLICATIONS

JIS Z 0237 : 2000 (Feb. 20, 2000).

(Continued)

*Primary Examiner* — Lisa Caputo
*Assistant Examiner* — Philip Cotey
(74) *Attorney, Agent, or Firm* — Porzio, Bromberg & Newman, P.C.

(57) ABSTRACT

A device for a peel test. The device includes: a gripping member to grip an end of a test film to be peeled off a test object; a movable member linearly moving in a direction to or away from the gripping member; a holding member for the movable member capable of linearly moving in a direction along a peel surface of the test object while holding the test object; a moving mechanism configured to move the movable member linearly; a load measuring unit configured to measure a load applied to the gripping member; a first conversion mechanism to convert the linear motion of the movable member to rotational power, and output the rotational power; and a second conversion mechanism to convert the rotational power output from the first conversion mechanism to the linear motion of the holding member relative to the movable member.

10 Claims, 8 Drawing Sheets

(56) References Cited

U.S. PATENT DOCUMENTS

| | | | |
|---|---|---|---|
| 5,847,284 A * | 12/1998 | Theller | 73/827 |
| 5,961,766 A * | 10/1999 | Chang et al. | 73/788 |
| 6,584,858 B1 * | 7/2003 | Miyazawa et al. | 73/150 R |
| 2001/0001371 A1 * | 5/2001 | Arrington et al. | 73/835 |
| 2002/0040608 A1 * | 4/2002 | Kamiya et al. | 73/862.334 |
| 2003/0015031 A1 * | 1/2003 | Nelson et al. | 73/150 A |
| 2005/0039534 A1 * | 2/2005 | Tokunaga et al. | 73/627 |
| 2005/0061065 A1 * | 3/2005 | Terpstra | 73/117 |
| 2008/0071409 A1 * | 3/2008 | Ahn et al. | 700/114 |
| 2008/0092709 A1 * | 4/2008 | Gaw | 83/473 |
| 2008/0202254 A1 * | 8/2008 | Deng et al. | 73/827 |
| 2009/0066322 A1 * | 3/2009 | Shintani et al. | 324/207.24 |
| 2009/0184598 A1 * | 7/2009 | Nakano et al. | 310/156.78 |
| 2010/0206057 A1 * | 8/2010 | Batchelder et al. | 73/105 |
| 2012/0023510 A1 * | 1/2012 | Ogawa | 720/621 |
| 2012/0123700 A1 * | 5/2012 | Tsaur | 73/150 A |

OTHER PUBLICATIONS

JIS Z 0237 : 2009 "Testing Methods of Pressure-Sensitive Adhesive Tapes and Sheets" (English Translation). Dec. 21, 2009.
JIS K 6854-1 : 1999 (Oct. 20, 1999).
JIS K 6854-21 : 1999 (Oct. 20, 1999).
JIS K 6854-3 : 1999 (Oct. 20, 1999).
JIS K 6854-4 : 1999 (Oct. 20, 1999).
JIS K 6854 : 1994 Testing methods for peel strength of adhesives (English Translation of JIS K 6854-1-2-3-4). Nov. 1, 1994.

* cited by examiner

DEVICE FOR PEEL TEST

BACKGROUND OF THE INVENTION

1. Field of the Invention

The present invention relates to a device for peel test used, for example, for testing the adhesive force of adhesive tapes or adhesive sheets, peel strength in the case of two bonded members, and the adhesive force of surface coatings formed by plating or the like.

2. Description of the Related Art

A peel test is a test method conventionally conducted to measure the adhesive force (sticking force) of adhesive tapes or adhesive sheets, and the peel strength of adhesive agents and the like. Examples of the peel test methods include a 90-degree peel test, a 180-degree peel test, a T-peel test, and a peel test with a floating roller. A 90-degree peel test and a 180-degree peel test applied as test methods for adhesive tapes or adhesive sheets are defined, for example, in JIS Z 0237. A 90-degree peel test, a 180-degree peel test, a T-peel test, and a peel test with a floating roller applied as test methods for adhesive agents are defined, for example, in JIS K 6854-1, 6854-2, 6854-3, and 6854-4 respectively.

The 180-degree peel test is largely affected by the strength or the degree of elasticity of a base material if it is applied for measuring an adhesive force such as that of an adhesive tape. Accordingly, the 90-degree peel test is considered as a preferred method of measuring such an adhesive force. However, the 90-degree peel test has found difficulty in maintaining a peel angle (angle formed between a test plate an adhesive tape sticks to and the adhesive tape being pulled) at 90 degrees all the time during the test. To be specific, the 90-degree peel test measures a load acting when a material such as an adhesive tape sticking to a test plate is pulled away from (peeled off) the test plate by pulling one end of the adhesive tape in a direction at an angle of 90 degrees to the test plate. A peel position moves transversely on the test plate as the adhesive tape is pulled away further, resulting in a problem of change of a peel angle.

A technique of transversely sliding a test plate with a dedicated jig for a distance corresponding to the peel length of a material such as an adhesive tape is introduced in JIS Z 0237 (see Non-Patent Literature 1). More specifically, this jig has an upper grip for gripping one end of a material such as an adhesive tape, and a lower grip for gripping a jig with a slidable test plate. The jig is configured such that, as the upper and lower grips are separated further from each other, the test plate is pulled with a string to move slidingly.

A technique that does not involve mechanical interlock of peeling of an adhesive tape and the sliding movement of a test plate is proposed (for example, in Patent Literature 1). This technique makes the sliding movement of a test plate with a material such as an adhesive tape sticking thereto with a stepping motor and a ball screw.

Patent Literature 1: Japanese Patent Application Laid-Open No. 9-113438

Non-Patent Literature 1: Japanese Industrial Standard JIS Z 0237

The technique of sliding a test plate with a string disclosed in Non-Patent Literature 1 mentioned above may generate a difference between a peel length and a sliding distance of the test plate due to flexure or stretch of the string, leading to a problem as a peel angle is changed during a test. In particular, a test plate may slide a distance longer than a peel length due to inertial force, or the test plate may vibrate violently if a peel test is conducted at a high speed. This results in a problem of considerable reduction of measurement accuracy.

The technique disclosed in Patent Literature 1 mentioned above requires driving units for driving a fixing part for fixing (gripping) an end of a material such as an adhesive tape and for driving a test plate, and also requires individual controls of the traveling speeds of the driving units. This results in a problem of the complex and high-cost structure of a measuring device.

SUMMARY OF THE INVENTION

The presenter invention has been made in view of the aforementioned current conditions. It is an object of the invention to provide a device for peel test capable of conducting a peel test simply and accurately.

(1) One aspect of the present invention is a device for peel test, including: a gripping member configured to grip an end of a test film to be peeled off a test object; a movable member capable of linearly moving in a direction in which the movable member goes closer to or away from the gripping member; a holding member provided to the movable member, and being capable of linearly moving in a direction along a peel surface of the test object while holding the test object; a moving mechanism configured to move the movable member linearly; a load measuring unit configured to measure a load applied to the gripping member; a first conversion mechanism configured to convert the linear motion of the movable member to rotational power, and output the rotational power; and a second conversion mechanism configured to convert the rotational power output from the first conversion mechanism to the linear motion of the holding member relative to the movable member.

(2) According to another aspect of the present invention, in the device for peel test described in the aforementioned (1), the first conversion mechanism includes a first rack extending in a direction in which the movable member moves, and a first pinion engaging with the first rack while being rotatably provided to the movable member.

(3) According to still another aspect of the present invention, in the device for peel test described in the aforementioned (1), the second conversion mechanism includes a second rack provided to the holding member to extend in a direction in which the holding member moves relative to the movable member, and a second pinion engaging with the second rack while being rotatably provided to the movable member.

(4) According to further another aspect of the present invention, the device for peel test described in the aforementioned (1) further includes a pivoting member configured to pivot the holding member relative to the movable member to change a peel angle at which the test film is peeled off the test object.

(5) According to still another aspect of the present invention, in the device for peel test described in the aforementioned (4), the pivoting member is configured such that the central axis of rotation of the pivoting member is substantially the same as a peel point at which the test film is peeled off the test object.

(6) According to further another aspect of the present invention, the device for peel test described in the aforementioned (1) further includes a transmission mechanism with a toothed belt or a chain through which the rotational power output from the first conversion mechanism is transmitted to the second conversion mechanism.

(7) According to another aspect of the present invention, the device for peel test described in the aforementioned (4) further includes a transmission mechanism with a toothed belt or a chain through which the rotational power output from the first conversion mechanism is transmitted to the second conversion mechanism, and the transmission mechanism transmits the rotational power output from the first conversion mechanism to the second conversion mechanism through an intermediary pulley or an intermediary sprocket coaxial with the central axis of rotation of the pivoting member.

(8) According to still another aspect of the present invention, the device for peel test described in the aforementioned (1) further includes a transmission mechanism with a rotation transmission shaft through which the rotational power output from the first conversion mechanism is transmitted to the second conversion mechanism.

(9) According to further another aspect of the present invention, the device for peel test described in the aforementioned (4) further includes a transmission mechanism with a rotation transmission shaft through which the rotational power output from the first conversion mechanism is transmitted to the second conversion mechanism, and the rotation transmission shaft is coaxial with the central axis of rotation of the pivoting member.

(10) According to still another aspect of the present invention, in the device for peel test described in the aforementioned (4) further includes a correction mechanism configured to correct the position shift of the holding member by converting the rotary motion of the pivoting member to the linear motion of the holding member relative to the movable member, with the position shift being generated during the rotation of the pivoting member.

The device for peel test according to the present invention achieves an excellent effect as the device is capable of conducting a peel test simply and accurately.

BRIEF DESCRIPTION OF THE DRAWINGS

FIGS. 6A and 5B are schematic diagrams showing an example where the device for peel test shown in FIGS. 5A and 5B is provided with a correction mechanism;

DETAILED DESCRIPTION OF THE PREFERRED EMBODIMENTS

An embodiment of the present invention will now be described below with reference to the accompanying drawings. It should be noted that teeth of gears and racks are not shown in the drawings.

Figure 1A:
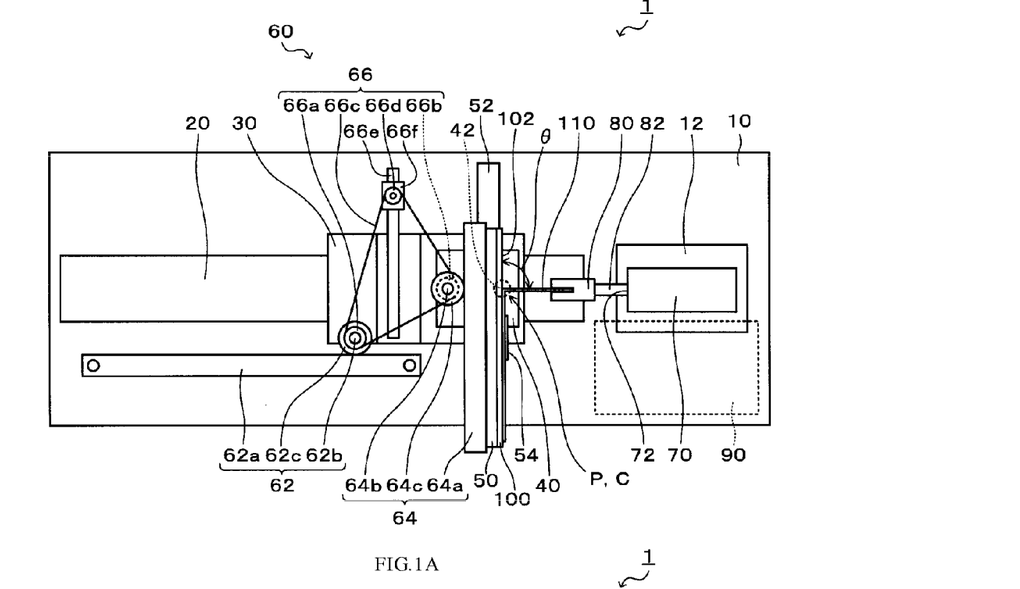
FIGS. 1A and 1B are schematic diagrams showing a device for peel test according to an embodiment of the invention.
Figure 1B:
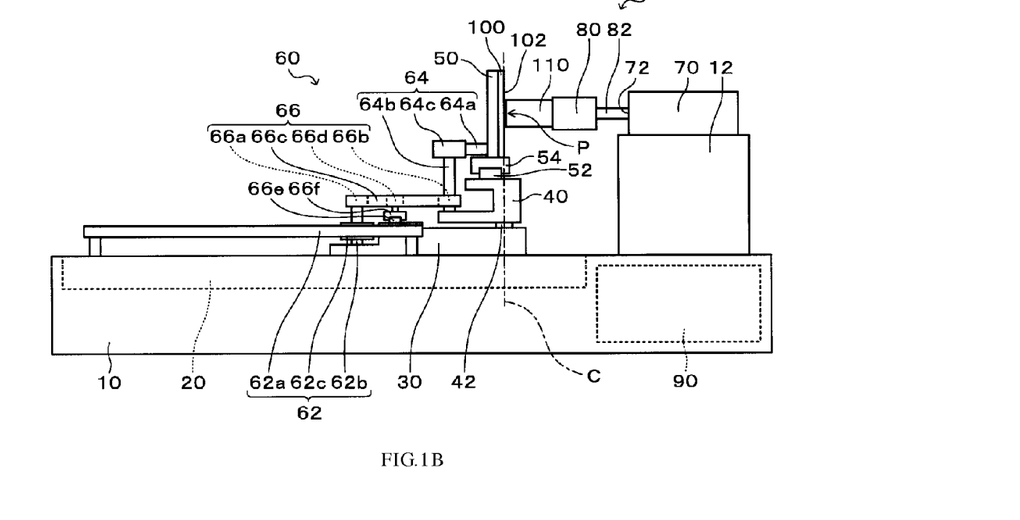

The structure of a device for peel test (peel testing device) 1 according to the embodiment of the present invention will be described first. FIGS. 1A and 1B are schematic diagrams showing the device for peel test 1 according to the embodiment. FIG. 1A is a plan view of the device 1 for peel test, and FIG. 1B is a front view of the same. The device for peel test 1 of the embodiment is intended to measure a force required for peeling a test film 110 that is, for example, an adhesive tape or a plated coating off a surface of a test object 100 in the form of a flat plate.

As shown in FIGS. 1A and 1B, the device 1 for peel test includes a base 10, a moving mechanism 20 arranged in an upper part of the base 10, a movable member 30 caused to linearly move by the moving mechanism 20, a pivoting member 40 that makes pivotal movement over the movable member 30, a holding member 50 that linearly moves over the pivoting member 40 while holding the test object 100, and a conversion mechanism 60 for converting the linear motion of the movable member 30 to the linear motion of the holding member 50. The device 1 for peel test also includes a load measuring unit 70 arranged on the base 10 such that the load measuring unit 70 faces the holding member 50, a gripping member 80 connected to the load measuring unit 70, the gripping member 80 holding an end of the test film 110 to be peeled off the test object 100, and a control unit 90 for controlling the entire device for peel test 1.

The base 10 supports the moving mechanism 20, the movable member 30, the load measuring unit 70 held on the base 10, and stores the control unit 90 inside the base 10. The shape of the base 10 is not specifically limited. The base 10 may be of any shape that can support the members in appropriate locations. A cover for covering the structure on the base 10 may be provided where appropriate.

The moving mechanism 20 causes the movable member 30 to linearly move back and forth in a direction (in a substantially horizontal direction in the present embodiment) in which the movable member 30 goes closer to or away from the gripping member 80. Although not shown, the moving mechanism 20 includes a linear guide for guiding the movement of the movable member 30, a ball screw transmission mechanism actuated by a stepping motor, and the like. The moving mechanism 20 is configured to be capable of causing the movable member 30 to move at any speed under control of the control unit 90, and capable of stopping the movable member 30 at any position. The moving mechanism 20 may be composed of any known parts/means including a linear motor, for example.

The movable member 30 supports the pivoting member 40 in a manner that allows the pivotal movement of the pivoting member 40. Further, the movable member 30 is actuated by the moving mechanism 20 to linearly move back and forth in a direction in which the movable member 30 goes closer to or away from the gripping member 80. Part of the conversion mechanism 60 described later is arranged on the movable member 30.

The pivoting member 40 supports the holding member 50 in a manner that allows the linear movement of the holding member 50. The pivoting member 40 is pivotably arranged over the movable member 30 through a pivotal shaft 42. More specifically, the pivoting member 40 is arranged such that the central axis C of rotation of the pivoting member 40 extends in a direction (in the present embodiment, a substantially vertical direction) substantially perpendicular to a direction in which the movable member 30 moves, and that the pivoting member 40 is configured to be capable of pivoting in a range of ±90 degrees (as described in more detail later). The pivoting member 40 is configured to be capable of being fixed with a known means such as a set screw after the pivoting member 40 rotates to an arbitrary angle. In the present embodiment, the pivotal movement of the pivoting member 40 makes it possible to set the peel angle θ of the test film 110 to the test object 100 at any angle of greater than zero degrees and less than, or equal to, 180 degrees.

The holding member 50 holds the test object 100 with a known means such as a clamp and a screw, and is disposed so as to be capable of linearly moving relative to the pivoting member 40. More specifically, the holding member 50 is configured to hold the test object 100 while a peel surface 102 at which the test film 110 is peeled off the test object 100 faces the gripping member 80. A guide rail 52 is arranged on the pivoting member 40 to extend in a direction (in the present embodiment, in a substantially horizontal direction) perpendicular to the central axis C of the pivoting member 40. The holding member 50 is arranged on a slider 54 that slidingly moves on the guide rail 52. Accordingly, the holding member 50 is configured to be capable of moving back and forth linearly along the guide rail 52 while holding the test object 100.

In the present embodiment, the linear movement of the holding member 50 relative to the pivoting member 40 and the movable member 30 keeps the peel angle θ at a constant angle during a test. To achieve this, the holding member 50 is configured to hold the test object 100 while the horizontal direction of the peel surface 102 extends along the guide rail 52 (parallel to the guide rail 52). Further, in the present embodiment, the peel angle θ can be set at any angle. To achieve this, the holding member 50 is configured to hold the test object 100 while the vertical direction of the peel surface 102 extends along (parallel to) the central axis C of rotation of the pivoting member 40. The slider 54 may be arranged on the pivoting member 40, and the guide rail 52 may be fixed to the holding member 50.

The conversion mechanism 60 converts the linear motion of the movable member 30 to the linear motion of the holding member 50 to cause the holding member 50 to move. The conversion mechanism 60 includes a first conversion mechanism for converting the linear motion of the movable member 30 to rotational power and outputting the rotational power, a second conversion mechanism 64 for converting the rotational power output from the first conversion mechanism 62 to the linear motion of the holding member 50 relative to the pivoting member 40 and the movable member 30, and a transmission mechanism 66 for transmitting the rotational power output from the first conversion mechanism 62 to the second conversion mechanism 64.

The first conversion mechanism 62 includes a first rack 62a that is a linear gear arranged above the base 10 to extend in a direction in which the movable member 30 moves, and a first pinion that is a gear engaging with the first rack 62a while being made rotatable above the movable member 30 by a first rotary shaft 62b. To be specific, the first conversion mechanism 62 causes the first pinion 62c to rotate by moving along the first rack 62a together with the movement of the movable member 30, thereby outputting the rotational power.

The second conversion mechanism 64 includes a second rack 64a that is a linear gear provided to the holding member 50 to extend in a direction in which the holding member 50 moves relative to the pivoting member 40, and a second pinion 64c that is a gear engaging the second rack 64a while being made rotatable above the pivoting member 40 by a second rotary shaft 64b. To be specific, the second conversion mechanism 64 causes the second pinion 64c to rotate by the rotational power transmitted from the first conversion mechanism 62 through the transmission mechanism 66 to make the linear movement of the second rack 64a, thereby causing the holding member 50 to linearly move relative to the pivoting member 40 and the movable member 30.

The transmission mechanism 66 is composed of a belt transmission mechanism. The transmission mechanism 66 includes a first pulley 66a connected to the first rotary shaft 62b to which the first pinion 62c is also connected, a second pulley 66b connected to the second rotary shaft 64b the second pinion 64c is also connected to, and a toothed belt (timing belt) 66c wound around the first and second pulleys 66a and 66b. To be specific, the transmission mechanism 66 is configured to transmit the rotational power output from the first rotary shaft 62b to the second rotary shaft 64b by belt driving.

The transmission mechanism 66 also includes a tension pulley 66d arranged above the movable member 30 so as to be capable of linearly moving, as a tension control mechanism for controlling the tension of the toothed belt 66c. The tension pulley 66d is arranged above the movable member 30 through a guide rail 66e and a slider 66f. The position of the tension pulley 66d above the movable member 30 relative to the first and second rotary shafts 62b and 64b can be changed.

The present embodiment adjusts the tension of the toothed belt 66c by changing the position of the tension pulley 66d. In the present embodiment, as described in more detail later, the pivotal movement of the pivoting member 40 to change the peel angle θ drastically changes a distance between the first and second rotary shafts 62b and 64b. Accordingly, the tension pulley 66d is configured to be movable in a relatively wide range.

The transmission mechanism 66 may also be composed of a chain transmission mechanism with a chain and a sprocket. Further, multiple tension pulleys 66d may be provided.

The load measuring unit 70 measures a load (pulling force) required to peel the test film 110 off the test object 100. In the present embodiment, the load measuring unit 70 is composed of a load cell. The load measuring unit 70 is arranged on a mount 12 formed on the base 10 to comply with the position of the test object 100 held by the holding member 50. The load measuring unit 70 is electrically connected to the control unit 90, and the output of the load measuring unit 70 is transmitted to the control unit 90. A detection method of a force by the load measuring unit 70 is not specifically limited. The load measuring unit 70 may detect a force in any method such as a strain gauge system, a piezoelectric system, a capacitive system, an electromagnetic system, and a turning fork system.

The gripping member 80 grips an open end of the test film 110, namely an end portion of the test film 110 not attached to the test object 100. The gripping member 80 is connected to a point of force application 72 of the load measuring unit 70 through a rod 82. In the present embodiment, the gripping member 80 grips an end portion of the test film 110 placed between two members. However, this is not the only structure of the gripping member 80, but the gripping member may be of a different structure. As an example, the gripping member 80 may engage in a hole formed in an end portion of the test film 110, or may fix the test film 110 with a screw.

The control unit 90 controls the operation of the moving mechanism 20. The control unit 90 also converts the output of the load measuring unit 70 to a load value, and outputs or stores the load value. The control unit 90 is configured to include a CPU, and storage means such as a ROM, a RAM, and a hard disk. Although not shown, the control unit 90 includes an operation panel for operating the device 1 for peel test, a display panel on which information of various types such as a test result is presented, and others.

The control unit 90 may be formed as a unit separate from the device 1 for peel test. A PC generally used may be used as the control unit 90. Or, the control unit 90 may be responsible only for the control of the moving mechanism 20. A test result from the load measuring unit 70 may be output to an external processing unit such as a PC.

Figure 2A:
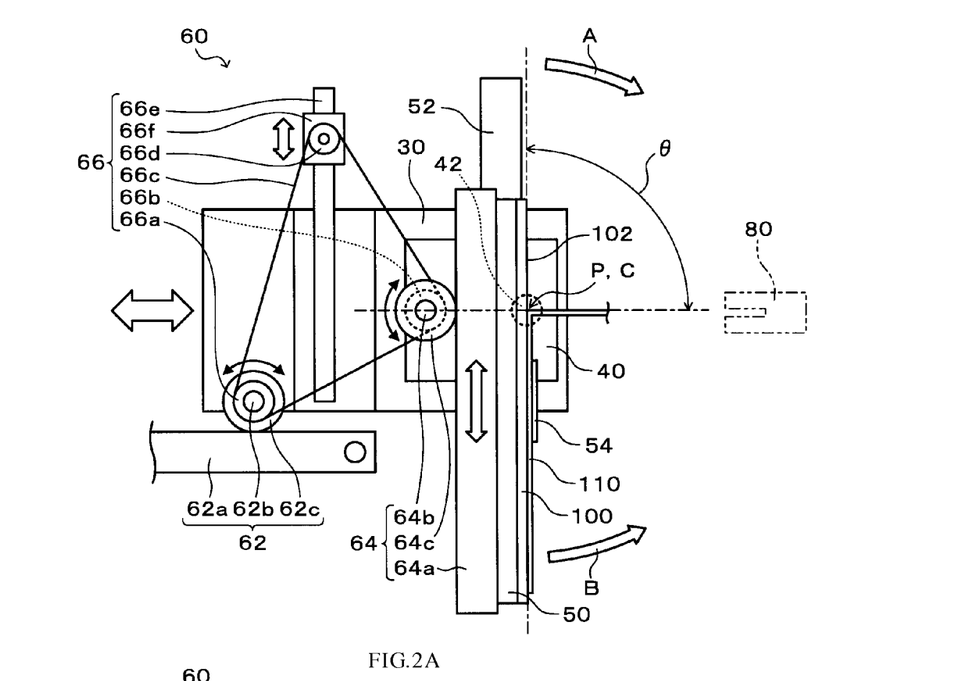
FIGS. 2A and 2B are schematic plan views showing a movable member and its vicinities in an enlarged manner.
Figure 2B:
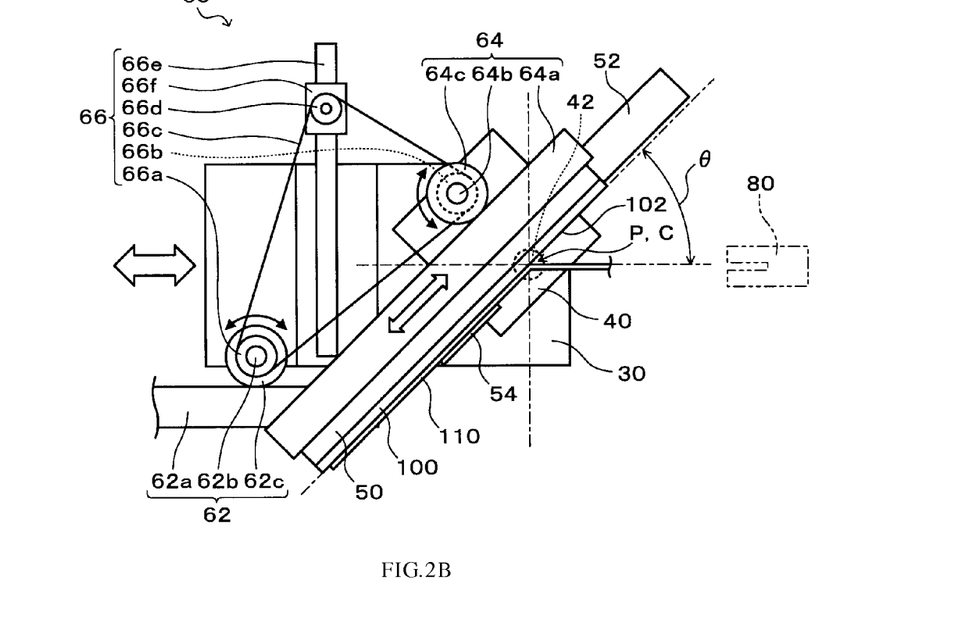

FIGS. 2A and 2B are schematic plan views showing the movable member 30 and its vicinities in an enlarged manner. The movement of the movable member 30 changes the position of the first pinion 62c relative to the first rack 62a, thereby causing the first pinion 62c to rotate. The resultant rotational power of the first pinion 62c is transmitted through the first pulley 66a and the toothed belt 66c to the second pulley 66b to cause the second pinion 64c to rotate. The rotation of the second pinion 64c causes the second rack 64a to move along the guide rail 52 together with the holding member 50, thereby causing the test object 100 to move along the peel surface 102.

The conversion mechanism 60 of the present embodiment includes the first and second pinions 62c and 64c with teeth in the same number and with the same tooth pitch, and the first and second pulleys 66a and 66b with teeth in the same number. Accordingly, in the present embodiment, the holding member 50 and the test object 100 move along the peel surface 102 a distance corresponding to the amount of movement of the movable member 30, namely a distance substantially the same as the peel length of the test film 110. This allows a peel point P at which the test film 110 is peeled off the test object 100 to be always in a direction during a test in which the gripping member 80 pulls the test film 110, meaning that the peel angle θ can always be constant during the test.

The first and second pinions 62c and 64c may have teeth in different numbers, or the first and second pulleys 66a and 66b may have teeth in different numbers in order for the conversion mechanism 60 to have a reduction gear ratio determined in consideration of the stretch of the test film 110.

As described above, the pivoting member 40 is configured to be capable of pivoting about the central axis C of rotation relative to the movable member 30. FIG. 2A shows the case where the peel angle θ is set at 90 degrees. In the present embodiment, the pivoting member 40 is configured to be capable of pivoting 90 degrees relative to the condition shown in FIG. 2A in a direction of arrow A of FIG. 2A (direction in which the peel angle θ is reduced), and in a direction of arrow B of FIG. 2A (direction in which the peel angle θ is increased). Accordingly, in the present embodiment, the peel angle θ during a test can be set at any angle of greater than zero degrees and less than, or equal to 180 degrees.

The structure of the present embodiment allows the peel angle θ to be set at zero degrees. However, the peel angle θ of zero degrees does not allow implementation of a test as it prevents the test film 110 from being peeled off the test object 100.

FIG. 2B shows the case where the peel angle θ is set at 45 degrees. The holding member 50 and the second conversion mechanism 64 pivot together with the pivoting member 40. Accordingly, even if the peel angle θ is changed by the pivotal movement of the pivoting member 40, the holding member 50 and the test object 100 still moves in a direction along the peel surface 102. This means that, irrespective of the setting of the peel angle θ, the present embodiment allows the test object 100 to move along the peel surface 102 a distance substantially the same as the peel length of the test film 110.

Changing the peel angle θ by causing the pivoting member 40 to pivot changes a distance between the axes of the first and second pulleys 66a and 66b as shown in FIGS. 2A and 2B. Meanwhile, in the present embodiment, the position of the tension pulley 66d is adjusted in response to the change of the peel angle θ, allowing the toothed belt 66c to be placed under appropriate tension even on the occurrence of the change of the peel angle θ. Thus, the present embodiment allows the peel angle θ to be changed to any angle of greater than zero degrees and less than, or equal to, 180 degrees without requiring exchange of the toothed belt 66c. Accordingly, the tension pulley 66d is capable of moving in a range responsive to the peel angle θ at any angle.

In the present embodiment, the pivotal shaft 42 is arranged such that the central axis C of rotation of the pivoting member 40 is substantially the same as the peel point P of the test film 110, namely that the central axis C of rotation nearly passes through the peel point P along a surface of the peel surface 102. Accordingly, substantially no change of the position of the peel point P is generated irrespective of the change of the peel angle θ. Thus, various conditions for a peel test such as the position of the test film 110 relative to the test object 100 can be set easily.

A procedure of a peel test conducted by using the device 1 for peel test will be described next.

Figure 3A:
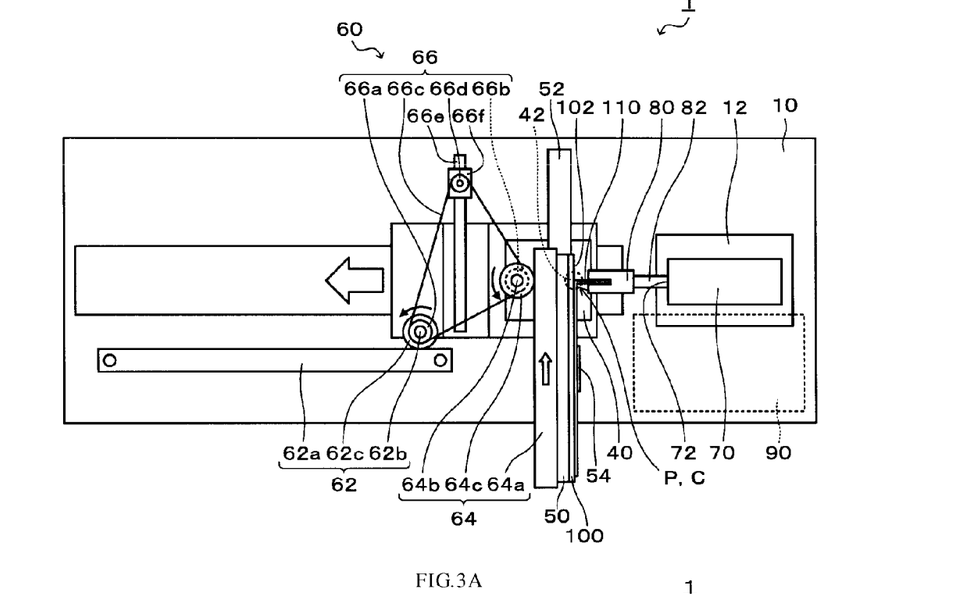
FIGS. 3A and 3B are schematic plan views showing how a peel test is conducted by the device for peel test.
Figure 3B:
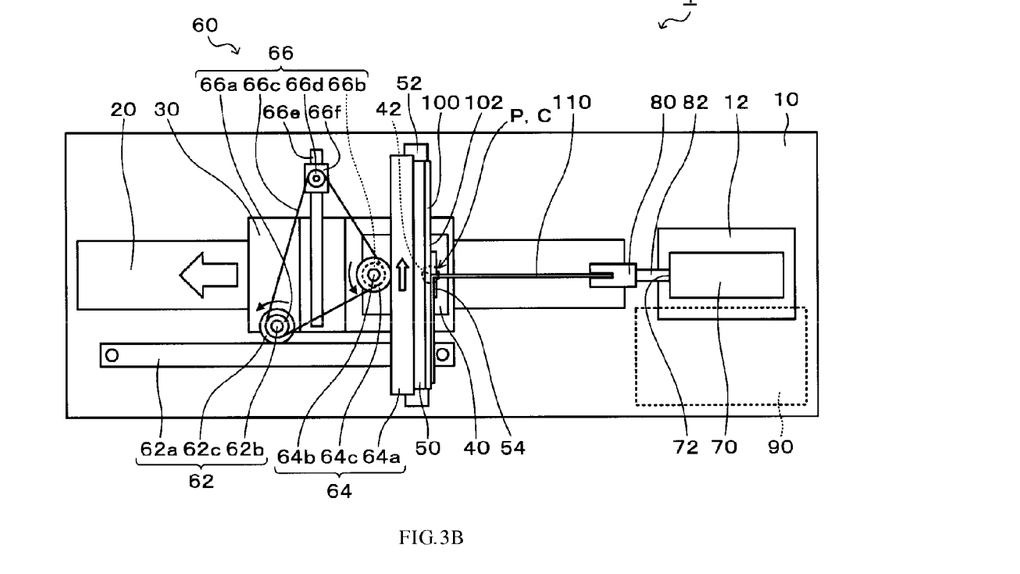

FIGS. 3A and 3B are schematic plan views showing how a peel test is conducted by the device 1 for peel test. First, in the peel test, the test object 100 with the test film 110 attached thereto is placed to be held by the holding member 50. The test film 110 may be an adhesive tape or an adhesive sheet sticking to the test object 100, or a coating formed on a surface of the test object 100 by plating, deposition, or spraying.

Next, the pivoting member 40 is caused to pivot to set the peel angle θ at a predetermined angle, and the tension pulley 66d is caused to move to place the toothed belt 66c under appropriate tension. FIGS. 3A and 3B show an example where the peel angle θ is set at 90 degrees. Then, the movable member 30 is caused to go closer to the gripping member 80 to make the gripping member 80 grip an open end of the test film 110.

The peel angle θ may be set manually or automatically. For the automatic setting of the peel angle θ, a driving unit such as a stepping motor may be provided to the movable member 30, and the pivotal movement of the pivoting member 40 may be controlled by the control unit 90. The tension pulley 66d may also be controlled manually or automatically.

Next, as shown in FIGS. 3A and 3B, the moving mechanism 20 causes the movable member 30 to move in a direction in which the movable member 30 goes away from the gripping member 80. At this time, the control unit 90 controls the moving mechanism 20 such that the movable member 30 is caused to move at a speed predetermined based on a test condition. Then, the load measuring unit 70 measures a pulling force applied to the gripping member 80.

The test film 110 is gradually peeled off the test object 100 in response to the movement of the movable member 30. Accordingly, the load measuring unit 70 measures a force required to peel the test film 110 off the test object 100. At this time, the conversion mechanism 60 causes the holding member 50 to move along the peel surface 102 at the same speed as the movable member 30, thereby keeping the peel angle θ at a constant angle during the test. The movable member 30 may move at a constant speed, or at varying speeds.

A result of measurement made by the load measuring unit 70 is stored as time-series data in the control unit 90, and if necessary, is output to a display panel or an external processing unit, for example. The peel test is finished once after following the aforementioned procedure.

In the present embodiment, the first and second conversion mechanisms 62 and 64 of the conversion mechanism 60 are each composed of a rack and pinion mechanism, and the transmission mechanism 66 is composed of a belt transmission mechanism with a toothed belt. This allows the movable member 30 and the holding member 50 to move in synchronization with each other quite stably and accurately, compared to a conventional device using a string and a pulley. To be specific, in the present embodiment the linear motion of the movable member 30 is converted once into to rotary motion, and transmits power reliably with little wobble or displacement by using gears and a toothed belt. This allows the movable member 30 and the holding member 50 to move in synchronization with each other more stably and more accurately than the case of the conventional example.

Thus, the device 1 for peel test of the present embodiment makes it possible to keep the peel angle θ accurately during the test, thereby allowing implementation of a peel test more accurately than conventional devices. Even if the movable member 30 is to move away from the gripping member 80 at a high speed, namely if the test film 110 is to be peeled off the test object 100 at a high speed, the holding member 50 is capable of moving stably in synchronization with the movable member 30. As a result, the device 1 for peel test can conduct a high-speed peel test accurately that has not been conducted easily by the conventional device.

Another form of the device 1 for peel test of will be described next. The description given below is intended only for a difference from the device 1 for peel test of the aforementioned example, and does not explain parts same as those of the device 1 for peel test of the aforementioned example.

Figure 4A:
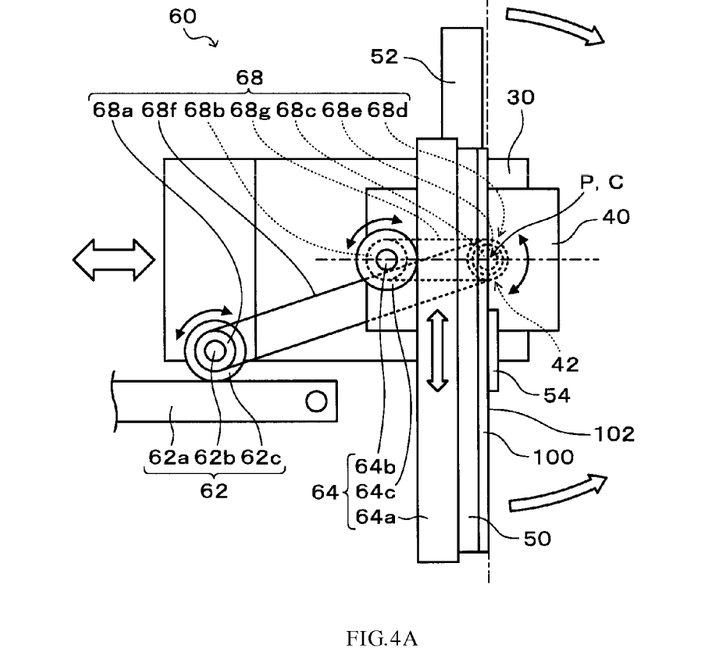
FIGS. 4A and 4B are schematic diagrams showing an example of the device for peel test in a different form.
Figure 4B:
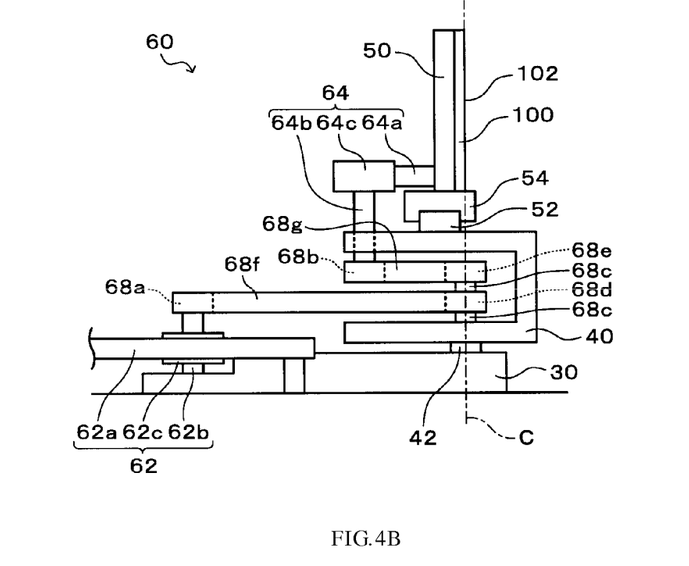

FIGS. 4A and 4B are schematic diagrams showing an example of the device 1 for peel test in the other form. FIGS. 4A and 4B are a plan view and a front view, respectively, that schematically show the movable member 30 and its vicinities in an enlarged manner. This example includes a transmission mechanism 68 as part of the conversion mechanism 60 and the transmission mechanism 68 is different from that of the aforementioned example. Further, the movable member 30 and the pivoting member 40 are of different shapes changed in response to the transmission mechanism 68.

The transmission mechanism 68 of this example includes a first pulley 68a connected to the first rotary shaft 62b the first pinion 62c is also connected to, a second pulley 68b connected to the second rotary shaft 64b the second pinion 64c is also connected to, an intermediary rotary shaft 68c coaxial with the central axis C of rotation and arranged on the pivoting member 40, and first and second intermediary pulleys 68d and 68e connected to the intermediary rotary shaft 68c. A first toothed belt 68f is wound around the first pulley 68a and the first intermediary pulley 68d, and a second toothed belt 68g is wound around the second intermediary pulley 68e and the second pulley 68b.

To be specific, the transmission mechanism 68 of this example transmits rotational power output from the first rotary shaft 62b to the intermediary rotary shaft 68c by belt driving through the first toothed belt 68f, and thereafter, transmits the rotational power from the intermediary rotary shaft 68c to the second rotary shaft 64b by belt driving through the second toothed belt 68g.

In this example, the intermediary rotary shaft 68c is coaxial with the central axis C of rotation of the pivoting member 40. Accordingly, if the peel angle θ is changed by causing the pivoting member 40 to pivot, a distance between the first rotary shaft 62b and the intermediary rotary shaft 68c, and a distance between the intermediary rotary shaft 68c and the second rotary shaft 64b are not changed. Thus, the change of the peel angle θ does not require readjustment of the tensions of the first and second toothed belts 68f and 68g, making it possible to change the peel angle θ more easily.

The belt transmission mechanism of this example may also be replaced by a chain transmission mechanism. The belt transmission mechanism of this example may be replaced by a gear transmission mechanism as a distance between the first rotary shaft 62b and the intermediary rotary shaft 68c, and a distance between the intermediary rotary shaft 68c and the second rotary shaft 64b are not changed. To be specific, rotational power output from the first rotary shaft 62b may be transmitted to the intermediary rotary shaft 68c through a first gear train, and thereafter, the rotational power may be transmitted from the intermediary rotary shaft 68c to the second rotary shaft 64b through a second gear train. If the gear transmission mechanism is employed, rotational power may be transmitted after a rotating direction is changed, for example, by a bevel gear, and may be transmitted through a rotating transmission shaft, and the like.

Figure 5A:
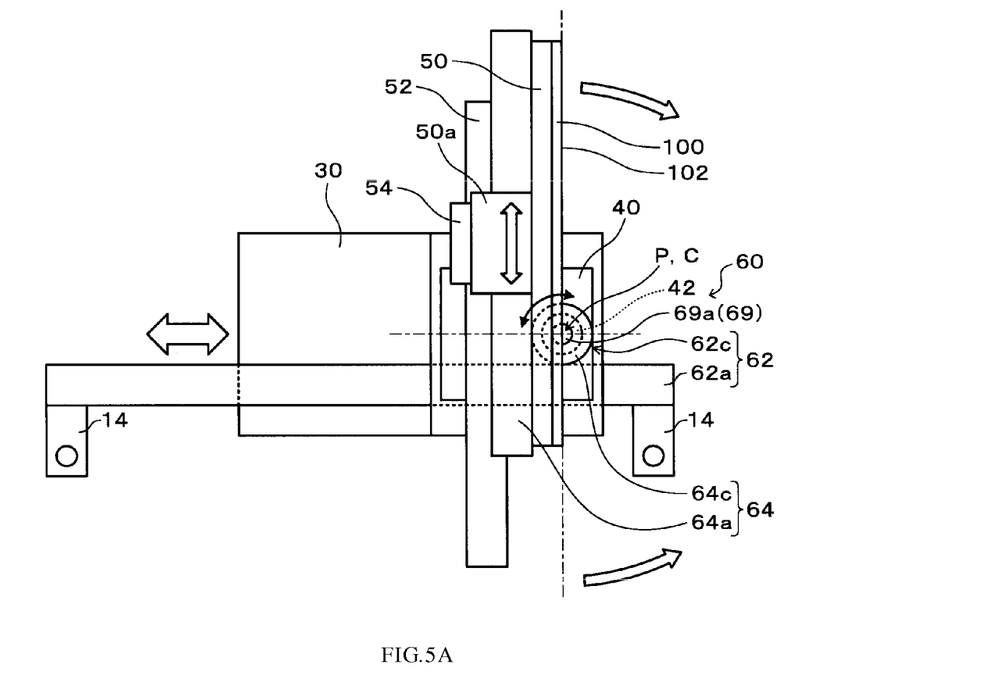
FIGS. 5A and 5B are schematic diagrams showing another example of the device for peel test in a different form.
Figure 5B:
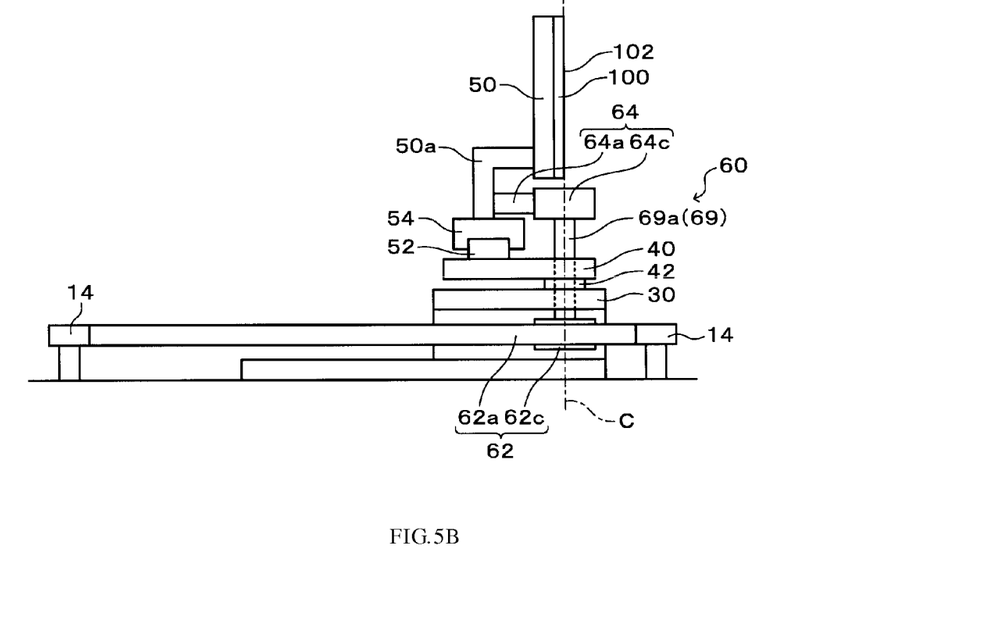

FIGS. 5A and 5B are schematic diagrams showing another example of the device 1 for peel test in a different form. FIGS. 5A and 5B are a plan view and a front view, respectively, that schematically show the movable member 30 and its vicinities in an enlarged manner. This example includes a transmission mechanism 69 as part of the conversion mechanism 60 and the transmission mechanism 69 is composed only of a rotation transmission shaft 69a. Further, the movable member 30, the pivoting member 40 and other members are of different shapes changed in response to the transmission mechanism 69.

In this example, the first conversion mechanism 62 is composed of the first rack 62a and the first pinion 62c, and the second conversion mechanism 64 is composed of the second rack 64a and the second pinion 64c. The transmission mechanism 69 is composed of the rotation transmission shaft 69a passing through the pivotal shaft 42 while being coaxial with the central axis C of rotation of the pivoting member 40. The first and second pinions 62c and 64c are connected to opposite end portions of the rotation transmission shaft 69a, respectively.

To be specific, in this example, the rotation of the rotation transmission shaft 69a is configured to directly transmit the rotational power of the first pinion 62c to the second pinion 64c. This structure allows the conversion mechanism 60 to have a considerably simple structure, while making it possible to cause the movable member 30 and the holding member 50 to move in synchronization with each other quite stably and accurately.

In this example, the holding member 50 is offset from the slider 54 through a connecting member 50a to prevent the interference of the holding member 50 with the second conversion mechanism 64. Further, the first rack 62a is offset toward the first pinion 62c through brackets 14c to prevent the interference of the first rack 62a with the movable member 30. The first rack 62a may not be offset, but the rotational power of the first pinion 62c may be transmitted through a gear train to the rotation transmission shaft 69a.

Figure 6A:
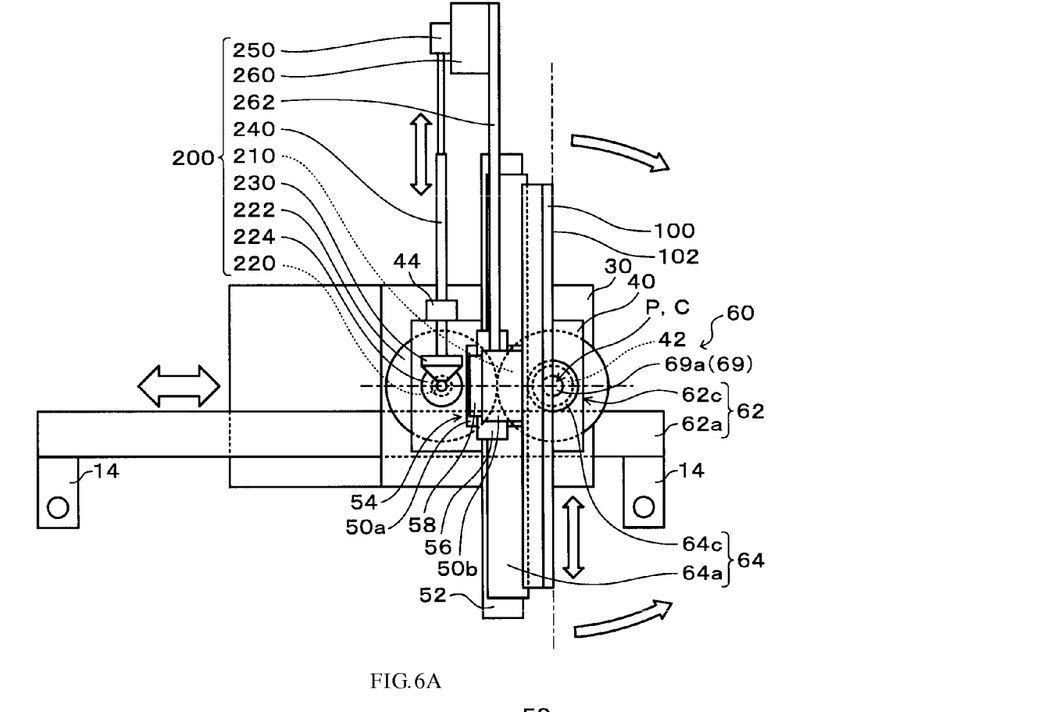
Figure 6B:
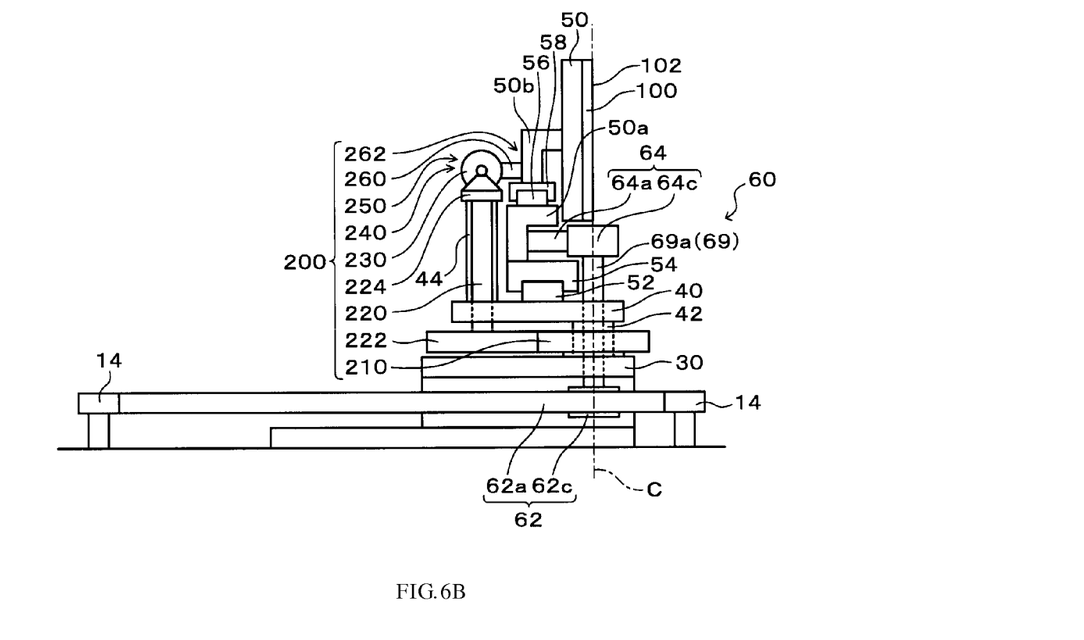

FIGS. 6A and 6B are schematic diagrams showing an example where the device 1 for peel test shown in FIGS. 5A and 5B is provided with a correction mechanism 200. FIGS. 6A and 6B are a plan view and a front view, respectively, that schematically show the movable member 30 and its vicinities in an enlarged manner.

In each of the examples described above, the rotation of the pivoting member 40 changes the position of the second rack 64a relative to the second pinion 64c to cause the holding member 50 to move, thereby slightly shifting the position of the test object 100. However, the example shown in FIGS. 6A and 6B includes the correction mechanism 200 that converts the rotary motion of the pivoting member 40 to the linear motion of the holding member 50 relative to the movable member 30, thereby correcting the position shift of the holding member 50.

In this example, the connecting member 50a is arranged on the slider 54, and the second rack 64a is provided to the connecting member 50a. A correction guide rail 56 and a correction slider 58 slidingly moving on the correction guide rail 56 are provided on the connecting member 50a. The holding member 50 is arranged above the correction slider 58 with a second connecting member 50b interposed between the holding member 50 and the correction slider 58.

The correction guide rail 56 extends in a direction substantially parallel to the guide rail 52. The correction slider 58 is movable in a direction in which the slider 54 moves, namely in a direction along the peel surface 102 of the test object 100 held by the holding member 50. Accordingly, in the example of FIGS. 6A and 6B, the holding member 50 and the test object 100 are capable of linearly moving back and forth along the peel surface 102 together with the slider 54, and capable of linearly moving back and forth along the peel surface 102 together with the correction slider 58 and independently of the movement of the slider 54.

The correction mechanism 200 is configured to convert the rotary motion of the pivoting member 40 to the linear motions of the correction slider 58 and the holding member 50 along the peel surface 102. The correction mechanism 200 includes: a stationary gear 210 arranged above the movable member 30; a planetary gear 222 rotatably provided to the pivoting member 40 through a first correction rotary shaft 220, the planetary gear 222 engaging with the stationary gear 210; a first bevel gear 224 connected to the first correction rotary shaft 220 the planetary gear 222 is also connected to; a second bevel gear 230 engaging with the first bevel gear 224; a second correction rotary shaft 240 with one end connected to the second bevel gear 230, the second correction rotary shaft 240 rotatably arranged above the pivoting member 40; a worm gear 250 connected to the other end of the second correction rotary shaft 240; and a worm rack 260 provided to the second connecting member 50b, the worm rack 260 engaging with the worm gear 250.

The stationary gear 210 is fixed in a manner that prevents the rotation of the stationary gear 210 over the movable member 30 about the central axis C of rotation of the pivoting member 40. The planetary gear 222 revolves around the stationary gear 210 while rotating in response to the pivotal movement of the pivoting member 40. To be specific, the stationary gear 210 and the planetary gear 222 convert the rotary motion of the pivoting member 40 to the rotational power of the first correction rotary shaft 220, and output the rotational power.

The first and second bevel gears 224 and 230 change the direction of the rotational power of the first correction rotary shaft 220, and transmit the rotational power to the second correction rotary shaft 240. The second correction rotary shaft 240 is rotatably journaled in a bearing 44 provided on the pivoting member 40. The second correction rotary shaft 240 is arranged to be substantially parallel to the guide rail 52 and the correction guide rail 56.

The worm gear 250 rotates together with the second correction rotary shaft 240 to cause the worm rack 260 to linearly move. The worm rack 260 is connected through an extension bracket 262 to the second connecting member 50b. Accordingly, in response to the linear movement of the worm rack 260, the holding member 50 and the test object 100 linearly move along the correction guide rail 56 together with the second connecting member 50b and the correction slider 58.

Figures 7A, 7B:
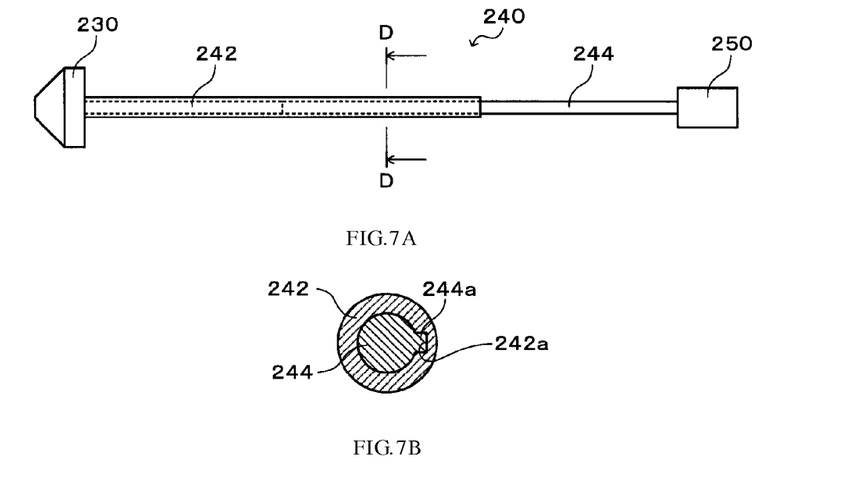
FIG. 7A are schematic diagrams showing the structure of a second correction rotary shaft.
FIG. 7B is a sectional view taken along line D-D of FIG. 7A.

FIG. 7A is a schematic diagram showing the structure of the second correction rotary shaft 240. FIG. 7B is a sectional view taken along line D-D of FIG. 7A. As shown in FIGS. 7A and 7B, the second correction rotary shaft 240 is composed of a cylindrical member 242, and a shaft member 244 in the form of a rod inserted into the cylindrical member 242. The second bevel gear 230 is connected to the cylindrical member 242, and the worm gear 250 is connected to the shaft member 244. The shaft member 244 is provided with a key 244a, and the cylindrical member 242 is provided with a key slot 242a the key 244a is fitted in.

To be specific, the second correction rotary shaft 240 is a telescopic member capable of transmitting rotational power. The second correction rotary shaft 240 allows for change of a distance between the second bevel gear 230 and the worm gear 250 while transmitting the rotational power of the second bevel gear 230 to the worm gear 250. In this example, since the second correction rotary shaft 240 is configured as above and the worm rack 260 is arranged to be spaced apart from the second connecting member 50b, it is possible to correct the position shift of the holding member 50 due to the pivotal movement of the pivoting member 40. The correction of this position shift does not affect the movement of the slider 54 and the holding member 50 to be caused by the conversion mechanism 60.

Figure 7C:
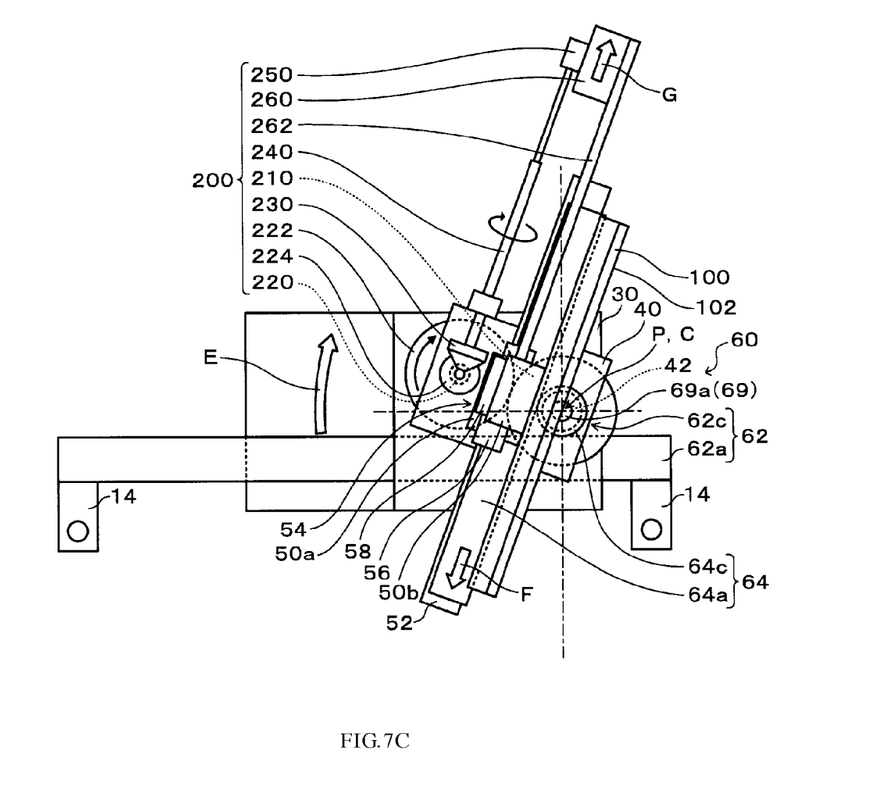
FIG. 7C is a schematic plan view showing how a correction mechanism is actuated in response to the pivotal movement of a pivoting member.

FIG. 7C is a schematic plan view showing how the correction mechanism 200 is actuated in response to the pivotal movement of the pivoting member 40. As shown in FIG. 7C, the pivotal movement of the pivoting member 40 in the direction of arrow E of FIG. 7C changes the position of the second rack 64a relative to the second pinion 64c, thereby causing the second rack 64a, the slider 54, and the connecting member 50a to move in the direction of arrow F of FIG. 7C.

In the correction mechanism 200, the planetary gear 222 revolves around the stationary gear 210 while rotating in response to the pivotal movement of the pivoting member 40. Rotational power generated as a result of the rotation of the planetary gear 222 is transmitted to the worm gear 250 through the first correction rotary shaft 220, the first and second bevel gears 224 and 230, and the second correction rotary shaft 240. Then, the worm gear 250 rotates to cause the worm rack 260 to move in the direction of arrow G of FIG. 7C, thereby causing the correction slider 58 and the second connecting member 50b to move in the direction of arrow G of FIG. 7C.

To be specific, the correction mechanism 200 is configured to cause the correction slider 58 and the second connecting member 50b to move in the direction opposite the direction in which the slider 54 and the connecting member 50a are caused to move in response to the pivotal movement of the pivoting member 40. A gear ratio reduced (or increased) from the stationary gear 210 to the worm rack 260 is suitably determined to control the amounts of movement of the correction slider 58 and the second connecting member 50b. By doing so, the positions of the holding member 50 and the test object 100 are not changed in response to the pivotal movement of the pivoting member 40. The second correction rotary shaft 240 extends or contracts during a peel test by following the movements of the second rack 64a, the slider 54, and the connecting member 50a caused by the conversion mechanism 60. This causes the holding member 50 and the test object 100 to move together with the second rack 64a, the slider 54, and the connecting member 50a, thereby keeping the peel angle θ at a constant angle during the test.

As described above, in the device 1 for peel test of this example, provision of the correction mechanism 200 prevents change of the positions of the holding member 50 and the test object 100 even on the occurrence of the pivotal movement of the pivoting member 40. Accordingly, various conditions for a peel test such as the position of the test film 110 relative to the test object 100 can be set more easily.

A member such as a stepping motor not shown for causing the pivoting member 40 to pivot may be provided to the movable member 30 together with the correction mechanism 200 to allow the pivoting member 40 to pivot while the movable member 30 moves. This allows a peel test to be conducted in an increased variety of styles. As an example, a peel test can be conducted while the peel angle θ is made variable by the pivotal movement of the pivoting member 40 during the peel test.

The correction mechanism 200 may use a face gear, a hypoid gear and the like in place of the first and second bevel gears 224 and 230. Or, the correction mechanism 200 may use a sliding screw transmission mechanism, a ball screw transmission mechanism, and the like in place of the worm gear 250 and the worm rack 260. The correction mechanism 200 may also use splines, serrations and the like in the second correction rotary shaft 240 in place of the key 244a. The device 1 for peel test shown in FIGS. 1 to 3, or the device 1 for peel test shown in FIG. 4 can certainly include the correction mechanism 200.

Figure 8:
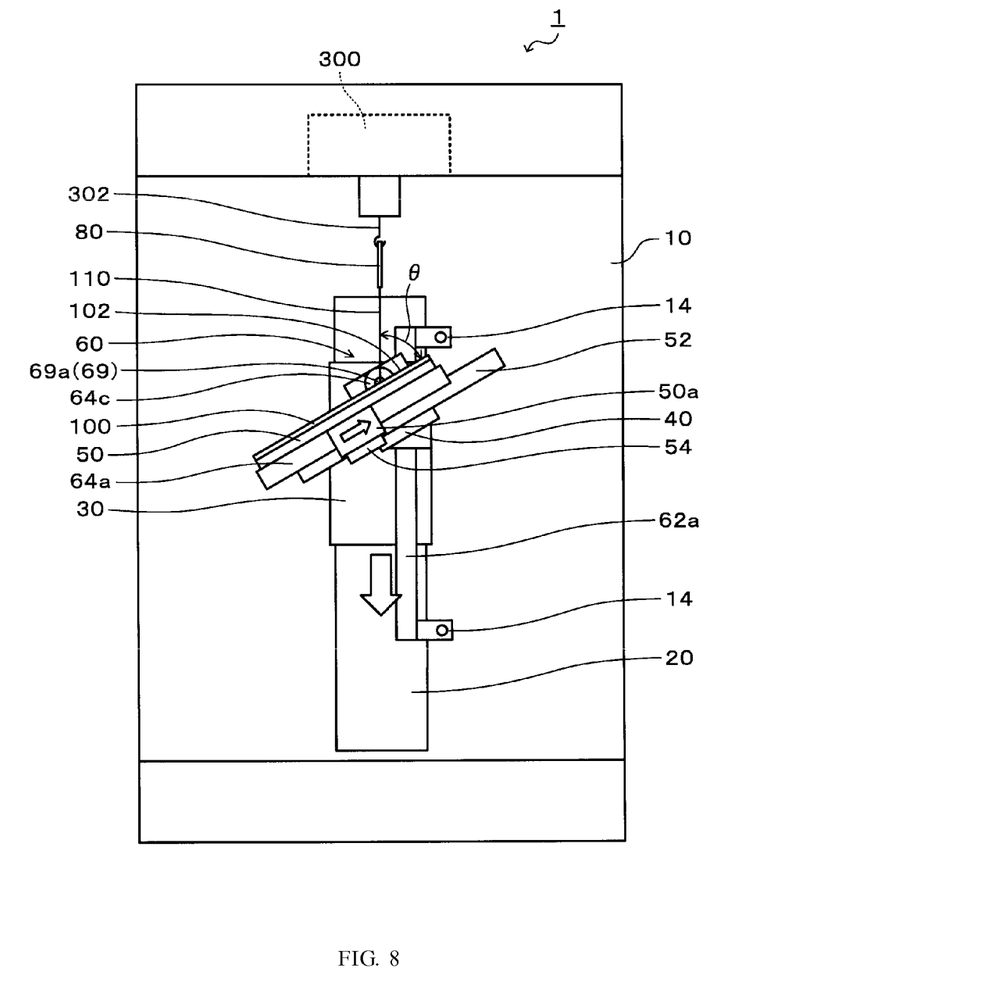
FIG. 8 is a schematic front view showing an example where the movable member is caused to move in a substantially vertical direction in the device for peel test shown in FIGS. 5A and 5B.

FIG. 8 is a schematic front view showing an example where the movable member 30 is caused to move in a substantially vertical direction in the device 1 for peel test shown in FIGS. 5A and 5B. The device 1 for peel test of this example includes an electrobalance 300 provided as a load measuring unit on the base 10. The gripping member 80 is connected to a hook 302 suspended from the electrobalance 300. The movable member 30 is arranged to linearly move up and down in the substantially vertical direction below the electrobalance 300.

Accordingly, the movable member 30 may move in the substantially vertical direction. The electrobalance 300 as a load measuring unit provided in this case allows measurement of smaller peel force accurately, allowing implementation of a peel test of the test object 100 and the test film 110 of varying materials the peel force of which cannot be measured by conventional devices.

The gripping member 80 may be suspended directly from the electrobalance 300, or may grip the test film 110 caught with the hook 302. The electrobalance 300 (or a load cell) may be arranged at a lower part of a base. In this case, the movable member 30 may linearly move up and down in the substantially vertical direction above the electrobalance 300 (or the load cell). The movable member 30 can certainly move in the substantially vertical direction in the device 1 for peel test shown in FIGS. 1 to 3, the device 1 for peel test shown in FIG. 4, or the device 1 for peel test shown in FIGS. 6 and 7.

As described above, the device 1 for peel test according to the present embodiment includes: the gripping member 80 configured to grip an end of the test film 110 to be peeled off the test object 100; the movable member 30 capable of moving linearly in a direction in which the movable member 30 goes closer to or away from the gripping member 80; the holding member 50 provided to the movable member 30, and being capable of linearly moving in a direction along the peel surface 102 of the test object 100 while holding the test object 100; the moving mechanism 20 configured to move the movable member 30 linearly; the load measuring unit 70 configured to measure a load applied to the gripping member 80; the first conversion mechanism 62 configured to convert the linear motion of the movable member 30 to rotational power, and output the rotational power; and the second conversion mechanism 64 configured to convert the rotational power output from the first conversion mechanism 62 to the linear motion of the holding member 50 relative to the movable member 30.

The aforementioned structure allows implementation of a peel test more simply and more accurately than conventional structures. In particular, conversion of the linear motion of the movable member 30 to rotational power and transmission of the rotational power allow the movable member 30 and the holding member 50 to move in synchronization with each other more stably and accurately than a conventional device using a string and a pulley, realizing implementation of a more accurate peel test than that conducted by the conventional device. Further, only control of the movement of the movable member 30 is required in order for the holding member 50 to move accurately along the peel surface 102 of the test object 100, so that a peel test can be conducted simply. The device 1 for peel test of the embodiment is also capable of conducting a high-speed peel test accurately that has not been conducted easily by conventional devices.

The first conversion mechanism 62 includes the first rack 62a extending in a direction in which the movable member 30 moves, and the first pinion 62c engaging with the first rack 62a while being rotatably provided to the movable member 30. This allows reliable power transmission with little wobble or displacement, so that the movable member 30 and the holding member 50 are capable of moving in synchronization with each other stably and accurately.

The second conversion mechanism 64 includes the second rack 64a provided to the holding member 50 to extend in a direction in which the holding member 50 moves relative to the movable member 30, and the second pinion 64c engaging with the second rack 64a while being rotatably provided to the movable member 30. This allows power transmission with little wobble or displacement, so that the movable member 30 and the holding member 50 are capable of moving in synchronization with each other stably and accurately.

The device 1 for peel test further includes the pivoting member 40 configured to pivot the holding member 50 relative to the movable member 30 to change the peel angle θ at which the test film 110 is peeled off the test object 100. This makes it possible to change the peel angle θ easily to conduct a peel test at the varying peel angle θ.

The pivoting member 40 is arranged such that the central axis C of rotation of the pivoting member 40 is substantially the same as the peel point P at which the test film 110 is peeled off the test object 100. This makes it possible to keep the peel point P at a substantially constant position irrespective of the value of the peel angle θ, so that a peel test can be conducted more simply.

The device 1 for peel test further includes the transmission mechanism 66 with the toothed belt 66c or a chain through which the rotational power output from the first conversion mechanism 62 is transmitted to the second conversion mechanism 64. This allows reliable power transmission with little wobble or displacement with a simple and low-cost structure, so that the movable member 30 and the holding member 50 are capable of moving in synchronization with each other stably and accurately.

The device 1 for peel test further includes the transmission mechanism 66 with the toothed belt 66c or a chain through which the rotational power output from the first conversion mechanism 62 is transmitted to the second conversion mechanism 64. The transmission mechanism 66 includes a tension control mechanism (tension pulley 66d) for controlling the tension of the toothed belt 66c or the chain if a distance between the first and second conversion mechanisms 62 and 64 changes in response to the pivotal movement of the pivoting member 40. This allows change of the peel angle θ without requiring exchange of the toothed belt 66c or the chain, so that the peel test can be conducted more easily at the varying peel angle θ.

The device 1 for peel test may further include the transmission mechanism 68 with a toothed belt (first and second toothed belts 68f and 68g) or a chain through which the rotational power output from the first conversion mechanism 62 is transmitted to the second conversion mechanism 64. The transmission mechanism 68 may transmit the rotational power output from the first conversion mechanism 62 to the second conversion mechanism 64 through an intermediary pulley (first and second intermediary pulleys 68d and 68e) or an intermediary sprocket coaxial with the central axis C of rotation of the pivoting member 40. Accordingly, the change of the peel angle θ does not require readjustment of the tension of the toothed belt or the chain, making it possible to change the peel angle θ more easily.

The device 1 for peel test may further include the transmission mechanism 69 with the rotation transmission shaft 69a through which the rotational power output from the first conversion mechanism 62 is transmitted to the second conversion mechanism 64. This allows reliable power transmission with substantially no wobble or displacement with a considerably simple and low-cost structure, so that the movable member 30 and the holding member 50 are capable of moving in synchronization with each other stably and accurately.

The device 1 for peel test may further include the transmission mechanism 69 with the rotation transmission shaft 69a through which the rotational power output from the first conversion mechanism 62 is transmitted to the second conversion mechanism 64. The rotation transmission shaft 69a may be coaxial with the central axis C of rotation of the pivoting member 40. This considerably simple and low-cost structure still allows the movable member 30 and the holding member 50 to move in synchronization with each other stably and accurately, while making it possible to change the peel angle θ easily.

The device 1 for peel test may further include the correction mechanism 200 configured to correct the position shift of the holding member 50 in response to the pivotal movement of the pivoting member 40 by converting the rotary motion of the pivoting member 40 to the linear motion of the holding member 50 relative to the movable member 30. The positions of the holding member 50 and the test object 100 are not shifted in response to the change of the peel angle θ, so that a more accurately peel test can be conducted more simply. Additionally, a peel test can be conducted in an increased variety of styles. As an example, a peel test can be conducted while the peel angle θ is variable.

The movable member 30 of the examples shown in the present embodiment is caused to move in a substantially horizontal or substantially vertical direction. However, the present invention is not limited thereto, and the movable member 30 may also be caused to move, for example, in a tilted direction. Further, the shapes and the locations of the respective elements of the device 1 for peel test including the movable member 30, the pivoting member 40, the holding member 50, and the conversion mechanism 60 are not limited to those shown in the examples of the embodiment. These elements may be of different shapes and at different locations where appropriate. The shape of the test object 100 is not limited to that shown in the present embodiment, but the test object 100 may be of a different shape.

The peel angle θ of the examples shown in the present embodiment can be changed by the pivoting member 40 provided to the movable member 30. However, the present invention is not limited thereto. The pivoting member 40 may be omitted to fix the peel angle θ at a certain angle.

The first and second conversion mechanisms 62 and 64 of the examples shown in the present embodiment are each composed of a rack and pinion mechanism. However, the present invention is not limited thereto, and the first and second conversion mechanisms 62 and 64 may each be composed of a different mechanism such as a sliding screw transmission mechanism, and a mechanism with a linearly extending chain and a sprocket. In some cases, a member such as a roller that makes rolling motion along a plane may take the place of the first and second pinions 62c and 64c.

The first and second pinions 62c and 64c of the examples shown in the present embodiment are arranged such that their central axes of rotation extend in a substantially vertical direction. However, the present invention is not limited thereto, and the first and second pinions 62c and 64c may also be arranged such that their axes of rotation extend in a different direction.

The pivoting member 40 of the examples shown in the present embodiment is arranged such that its central axis C of rotation extends in a substantially vertical direction. However, the present invention is not limited thereto. The pivoting member 40 can be arranged such that the central axis C of rotation of the pivoting member 40 may extend in a different direction as long as the holding member 50 is allowed to move in a direction substantially perpendicular to the central axis C of rotation.

The central axis C of rotation of the pivoting member 40 of the examples shown in the present embodiment is substantially the same as the peel point P. However, the present invention is not limited thereto, and the central axis C of rotation may be in a position shifted from the peel point P. This may result in more efficient layout over the movable member 30.

The device for peel test of the present invention is not limited to the embodiment of the invention described above, but changes can certainly be added to the device for peel test of the invention without departing from the scope of the invention.

The device for peel test of the present invention is widely applicable in the field of peel tests with various targets of peel such as members attached to test objects, for example, by bonding, coating materials, and platings.

The entire disclosure of Japanese Patent Application No. 2010-245282 filed on Nov. 1, 2010 including specification, claims, drawings, and summary are incorporated herein by reference in its entirety.

What is claimed is:
1. A device for peel test, comprising:
a gripping member configured to grip an end of a test film to be peeled off a test object;
a movable member capable of linearly moving in a direction in which the movable member moves closer to or away from the gripping member;
a holding member provided to the movable member, and being capable of linearly moving in a direction along a peel surface of the test object while holding the test object;
a moving mechanism configured to move the movable member linearly;
a load measuring unit configured to measure a load applied to the gripping member;
a first conversion mechanism configured to convert a linear motion of the movable member to rotational power, and output the rotational power; and a second conversion mechanism configured to convert the rotational power output from the first conversion mechanism to a linear motion of the holding member relative to the movable member.

2. The device for peel test according to claim 1, wherein the first conversion mechanism includes a first rack extending in a direction in which the movable member moves, and a first pinion engaging with the first rack while being rotatably provided to the movable member.

3. The device for peel test according to claim 1, wherein the second conversion mechanism includes a second rack provided to the holding member to extend in a direction in which the holding member moves relative to the movable member, and a second pinion engaging with the second rack while being rotatably provided to the movable member.

4. The device for peel test according to claim 1, further comprising a pivoting member configured to pivot the holding member relative to the movable member to change a peel angle at which the test film is peeled off the test object.

5. The device for peel test according to claim 4, wherein the pivoting member is configured such that a central axis of rotation of the pivoting member is substantially the same as a peel point at which the test film is peeled off the test object.

6. The device for peel test according to claim 1, further comprising a transmission mechanism with a toothed belt or a chain through which the rotational power output from the first conversion mechanism is transmitted to the second conversion mechanism.

7. The device for peel test according to claim 4, further comprising a transmission mechanism with a toothed belt or a chain through which the rotational power output from the first conversion mechanism is transmitted to the second conversion mechanism, and wherein the transmission mechanism transmits the rotational power output from the first conversion mechanism to the second conversion mechanism through an intermediary pulley or an intermediary sprocket coaxial with the central axis of rotation of the pivoting member.

8. The device for peel test according to claim 1, further comprising a transmission mechanism with a rotation transmission shaft through which the rotational power output from the first conversion mechanism is transmitted to the second conversion mechanism.

9. The device for peel test according to claim 4, further comprising a transmission mechanism with a rotation transmission shaft through which the rotational power output from the first conversion mechanism is transmitted to the second conversion mechanism, and wherein the rotation transmission shaft is coaxial with the central axis of rotation of the pivoting member.

10. The device for peel test according to claim 4, further comprising a correction mechanism configured to correct a position shift of the holding member by converting the rotary motion of the pivoting member to the linear motion of the holding member relative to the movable member, with the position shift being generated during the rotation of the pivoting member.

* * * * *